US00PP10648P

United States Patent [19]

Olesen et al.

[11] Patent Number: Plant 10,648

[45] Date of Patent: Oct. 20, 1998

[54] ROSE PLANT NAMED 'POULCOV'

[75] Inventors: L. Pernille Olesen; Mogens N. Olesen, both of Fredensborg, Denmark

[73] Assignee: Poulsen Roser APS, Fredensborg, Denmark

[21] Appl. No.: 779,607

[22] Filed: Jan. 7, 1997

[51] Int. Cl.[6] ..... A01H 5/00

[52] U.S. Cl. ..... Plt./1

[58] Field of Search ..... Plt./1, 3, 23

[56] References Cited

PUBLICATIONS

UPOVROM, 1997 Mar., "Plant Variety Database", GTI Jouve Retrieval Software, 7 Citations for Cultivar Name 'POULcov'.

*Primary Examiner*—Howard J. Locker

*Attorney, Agent, or Firm*—Foley & Lardner

[57] ABSTRACT

A new and distinct cultivar of shrub rose plant named 'POULcov', characterized by its compact and spreading habit; abundant white flowers with clean, semi-double blooms which cover the plant; continuous flowering from first flush through first frost; excellent disease resistance with healthy green foliage and good winter hardiness.

1 Drawing Sheet

The present invention comprises a new and distinct cultivar of rose plant of the compact shrub (landscape rose) class, hereinafter referred to by the cultivar name 'POULcov'.

'POULcov' is a product of a planned breeding program having the objective of creating new rose cultivars which have improved disease resistance, flower continuously from first flush to first frost, improved winter hardiness, and require limited maintenance. This combination of traits required improvement in commercial cultivars of this type.

'POULcov' was originated from a hybridization made in controlled breeding program in Fredensborg, Denmark in 1985. The female and male parents were unnamed proprietary Poulsen Roser ApS seedlings.

'POULcov' was discovered and selected as one flowering plant within the progeny of the stated parentage by L. Pernille and Mogens N. Olesen on Jul. 1, 1986 in a controlled environment in Fredensborg, Denmark.

Asexual reproduction of the new cultivar by budding and cutting, as performed by Pernille and Mogens Olesen on Aug. 1, 1986 in Fredensborg, Denmark, has demonstrated that the combination of characteristics, as herein disclosed for 'POULcov', are firmly fixed through successive generations of asexual reproduction.

'POULcov' has not been observed under all possible environmental conditions. The phenotype may vary significantly with variations in environment, such as temperature, light intensity, and day length, without a change in genotype of the variety. The following observations, measurements and comparisons describe plants grown in Fredensborg, Denmark and Appelgate, Jackson County, Oreg. U.S.A. under nursery conditions which approximate those generally used in commercial practice.

The following traits have been repeatedly observed and are determined to be basic characteristics of 'POULcov', which in combination, distinguish this rose as a new and distinct cultivar:

1. shrub rose with a compact and spreading habit;
2. abundant, white flowers with clean semi-double blooms which cover the plant;
3. continuous flowering from first flush through first frost;
4. excellent disease resistance with healthy green foliage;
5. spreading habit and good disease resistance allows for use of the variety as a landscape plant along highways and in areas of limited care;
6. good winter hardiness; and 7. ability to grow as "own root" plant in plantings.

Of the many commercial cultivars known to the present inventors, the most similar in comparison to 'POULcov' is 'POULemb', which is protected under U.S. Plant Pat. No. 9,650, Chart A compares certain characteristics of 'POULcov' to those same characteristics of 'POULemb'.

CHART A

| Characteristic | 'POULcov' | 'POULemb' |
|---|---|---|
| Flower color | Pure white with yellow center | White with yellow center |
| Flower type | Semi-double | Single |
| Flower size - open | to 1½" (38 mm) | to 1" (25 mm) |
| Foliage appearance | Slightly glossy | Glossy |
| Plant size (9 months after planting 2 yr bushes) | 40 cm (height) × 100 cm (width) | 40 cm (height) × 100 cm (width) |
| Foliage size | Foliage larger than 'POULemb' | Foliage smaller than 'POULcov' |
| Stems | Canes thicker and stronger than 'POULemb' | Canes thinner than 'POULcov' |

In general comparison to 'POULemb', 'POULcov' produces larger flowers, semi-double-type flowers and less pronounced yellow center (including floral parts) in completely open blooms.

The accompanying color photographic drawing shows typical inflorescence, foliage and stem characteristics of 'POULcov', with the colors being as nearly true as possible with illustrations of this type. The specimen shown in the photograph was grown in Appelgate, Jackson County, Oreg. and the photograph was taken in Sep. 1996. The photograph shows the main stem of a specimen with lateral and terminal flowers (right); flowers at various stages of development, including a fully open flower (left); and top and bottom views of the leaves.

In the following description, color references are made to The Royal Horticultural Society Colour ("RHS") Chart. The color values were determined at about noon on Jul. 1, 1987 under normal summer light conditions in Fredensborg, Denmark.

Classification:

*Botanical.*—*Rosa hybrida.*

*Commercial.*—Compact shrub rose.

Plant:

*General appearance.*—Habit: Compact, spreading Growth: Plants budded on *R. multiflora* understock grow moderately to vigorously with growth mostly lateral to upright-lateral to form plants that are uniform and bushy. Canes: Moderately vigorous with large lateral growth. Mostly green in color; younger stem is 138C R.H.S. and older stem is 138A R.H.S. Main Stems: From bud union to ½" (12 mm) the stems are semi-woody. Thorns: Moderate to few thorns. The upper edge of the thorns is slightly convex, while the lower edge is concave. Older thorns are brown to brown-black in color (200D R.H.S.). Younger thorns are red to reddish brown and black in color (178B R.H.S.). The thorns measure up to 6 mm in length. Branches: Predominantly lateral and upwardly growing.

*Foliage.*—Leaves: Number: Abundant, commonly with 3–7 leaflets. Shape: Leaflets are ovate in shape. The base of the terminal leaflet is obtuse, while leaf tip of terminal leaflet is acute to broadly acuminate. Width: 30–50 mm. Length: 80–100 mm. Appearance: Slightly glossy with extremely fine or nearly absent serration of edge. Color (juvenile foliage): 139A R.H.S. Color (top side): Medium green (141B R.H.S.) Color (bottom side): Medium green (143C R.H.S.) Stipules: Generally present on all leaves measuring to approximately ⅝" (16 mm) in length and green in color (138A R.H.S.). Other foliage characteristics: Leaf size small to very small.

Flowers:

*Borne.*—Single and in clusters from terminal bud. Single from upper most lateral buds.

*Type of stems.*—Semi-upright with multiple branching.

*Rachis color.*—141A R.H.S.

*Number of flowers* (*per stem*).—An entire flowering stem may have 6–10 lateral flowering shoots, each with 1–4 flowers. The entire stem can have as many as 15–25 flowers and buds.

*Quantity of blooms.*—Continual flowering from first flush to frost with abundant flowers.

*Buds.*—Peduncle color: 139A R.H.S. Peduncle length: ¾ to 1" (19–25 mm). Peduncle surface: Smooth. Peduncle strength: Good. Bud shape: Ovate. Bud color: White (155D R.H.S.); with cool night temperatures the exterior petals may have a red blush (49A R.H.S.) that fades as the flower opens. Receptacle color: Light green (143D R.H.S.). Receptacle shape: Pitcher-shaped and small. Receptacle surface: Smooth. Sepal color: Light green (143D R.H.S.). Sepal surface texture: Lightly pubescent.

*Blooms.*—Continuously present from first flush until first frost. Size: Open flowers measure up to approximately 1½" (38 mm) in width. Petalage (single, double, etc.): Semi-double with 10–15 somewhat reflexed petals. Petal edges are smooth. Length: Bud measures up to approximately ⅝" (16 mm) in length. Texture: Smooth. Shape: Open flower shape is flat. Color: Upperside: No spot at base. White (155D R.H.S.). Underside: White (155D R.H.S.). With cool nighttime temperatures the exterior petals have some red blush which generally fades upon opening.

*Fragrance.*—None.

*Reproductive organs.*—Stamens: Visible on open blooms, abundant and predominantly yellow (15C R.H.S.). Filaments: Predominantly white. Anthers: Predominantly yellow (15C R.H.S.). Pollen: Yellow (15C R.H.S.). Pistils: Shorter in length than the stamens. Styles: Predominantly yellow green and slightly pubescent. Ovaries: Half inferior. Hips: Generally few and if present, small. Seed: Limited seed set.

Disease resistance: 'POULcov' has demonstrated excellent disease resistance to black spot, powdery mildew, downy mildew, and rose rust.

We claim:

1. A new and distinct cultivar of rose plant named 'POULcov', as illustrated and described.

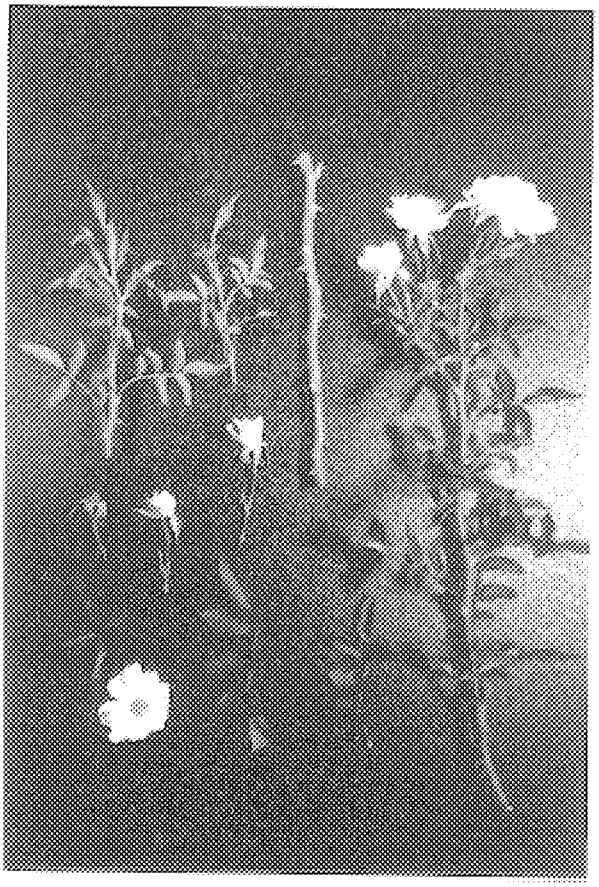

* * * * *